(12) United States Patent
Nagata et al.

(10) Patent No.: US 6,496,018 B1
(45) Date of Patent: Dec. 17, 2002

(54) METHOD AND DEVICE FOR MEASURING DIELECTRIC CONSTANT

(75) Inventors: Shinichi Nagata, Hyogo-ken (JP); Seiichi Miyamoto, Hyogo-ken (JP); Fumiaki Okada, Kamakura (JP)

(73) Assignee: Oji Paper Co., Ltd., Tokyo-To (JP)

( * ) Notice: Subject to any disclaimer, the term of this patent is extended or adjusted under 35 U.S.C. 154(b) by 0 days.

(21) Appl. No.: 09/787,410

(22) PCT Filed: Sep. 27, 1999

(86) PCT No.: PCT/JP99/05234

§ 371 (c)(1),
(2), (4) Date: Jun. 7, 2001

(87) PCT Pub. No.: WO00/19186

PCT Pub. Date: Apr. 6, 2000

(30) Foreign Application Priority Data

Sep. 25, 1998 (JP) .............................. 10-271348

(51) Int. Cl.[7] .............................................. G01R 27/04
(52) U.S. Cl. ...................................... 324/636; 324/632
(58) Field of Search .............................. 324/635, 636, 324/632, 644

(56) References Cited

U.S. PATENT DOCUMENTS 5,072,172 A * 12/1991 Stolarczyk .................. 324/635
5,239,269 A * 8/1993 Martens ..................... 324/632
5,397,993 A * 3/1995 Tews .......................... 324/632

FOREIGN PATENT DOCUMENTS

| JP | 49-11195 | 1/1974 |
|---|---|---|
| JP | 53-6091 | 1/1978 |
| JP | 56-40787 | 9/1981 |
| JP | 57-52534 | 11/1982 |
| JP | 2-272349 | 11/1990 |
| JP | 7-103917 | 4/1995 |
| JP | 7-225200 | 8/1995 |
| JP | 10-507263 | 7/1998 |
| JP | 10-325811 | 12/1998 |
| WO | WO00/19186 | 6/2000 |

* cited by examiner

*Primary Examiner*—Christine Oda
(74) *Attorney, Agent, or Firm*—Rader, Fishman & Grauer, PLLC

(57) ABSTRACT

The sample measuring face of a dielectric resonator (20) is placed near a standard sample having a known dielectric constant at a fixed interval D. While appropriately varying the dielectric constant and thickness of the standard sample under the above condition, the variation of the resonance frequency of the dielectric resonator (20) is measured for each varied dielectric constant and thickness to draw a calibration curve of the varied resonance frequency depending on the dielectric constant and thickness. Under the same condition where calibration curve is drawn, the variation of the resonance frequency of the dielectric resonator (20) for a sample having a known thickness is measured. The dielectric constant of the sample is found from the measurement value and the calibration curve. The dielectric constant of not only a sheetlike sample but also a three-dimensional molded article or a liquid sample can be measured easily.

12 Claims, 18 Drawing Sheets

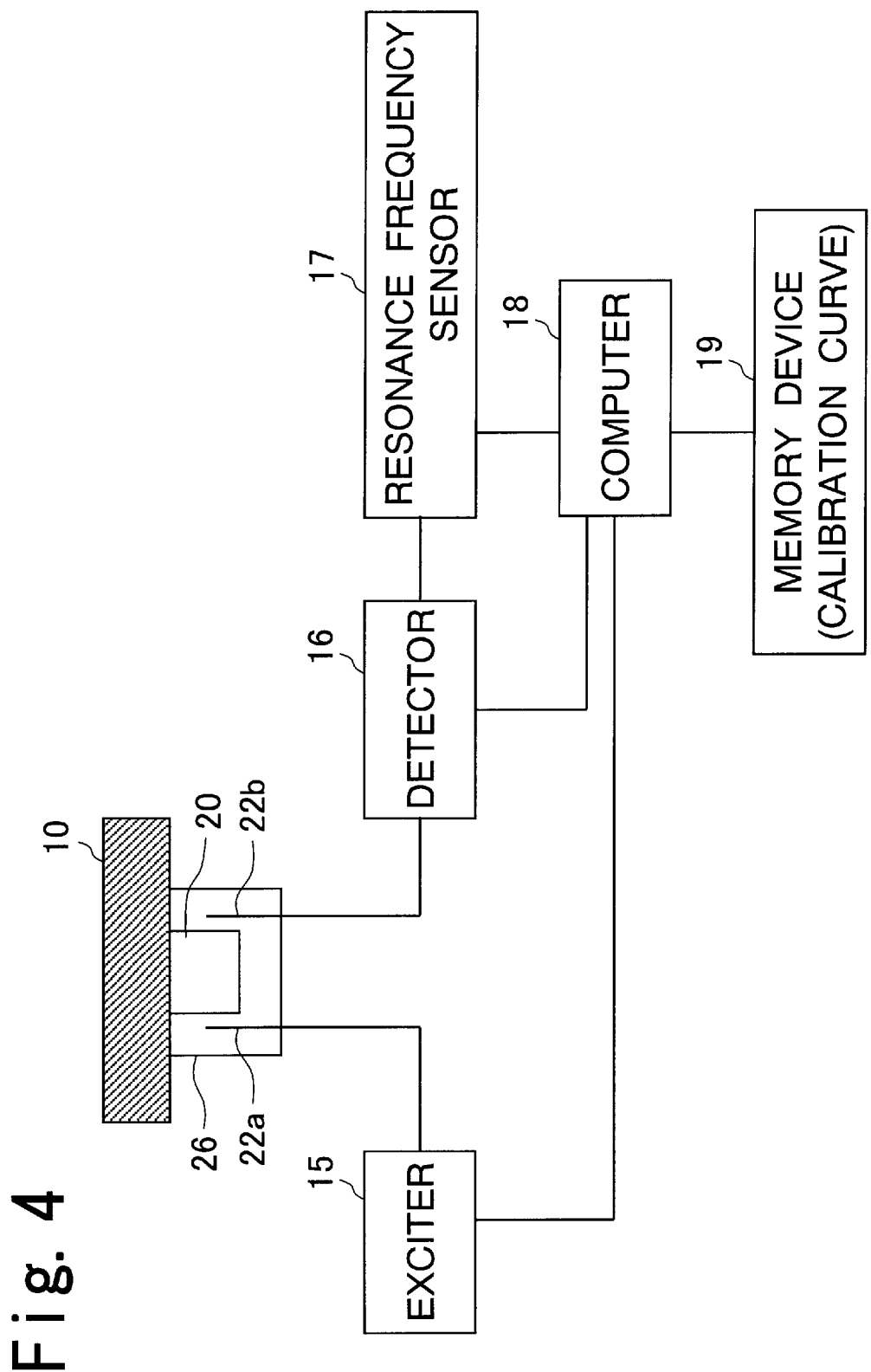

Fig.15(A) FIELD DISTRIBUTION ($TM_{201}$ MODE)
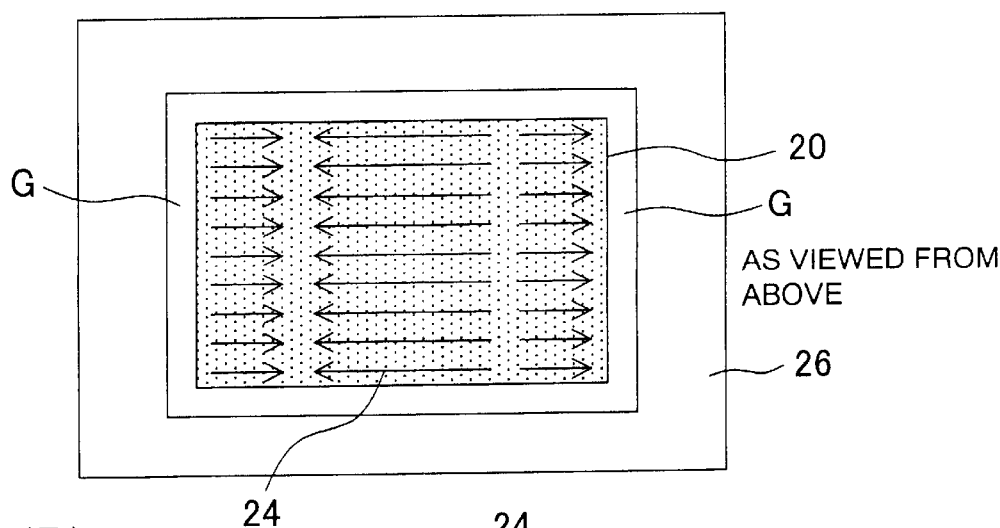
AS VIEWED FROM ABOVE
Fig.15(B)
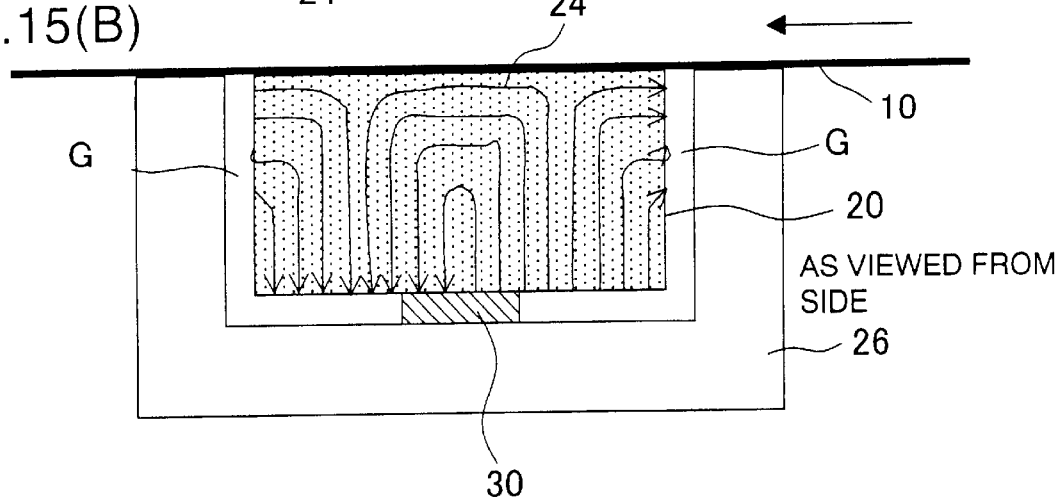
AS VIEWED FROM SIDE

METHOD AND DEVICE FOR MEASURING DIELECTRIC CONSTANT

TECHNICAL FIELD

The present invention relates to a method and a device for measuring dielectric constants by microwaves, of sheetlike substances such as a high-polymer sheet and paper including film, and three-dimensional articles such as moldings of plastic, resin, rubber and the like, as well as liquids such as an aqueous solution, a water dispersion liquid, an organic solvent liquid, liquid organic matter and the like.

TECHNICAL BACKGROUND

A dielectric constant is a physical value based on polarization in the inner part of a substance similar to a refractive index, and considered as an important physical value since the same is closely connected with electric, optical and dynamic physical properties. In a high-frequency domain such as light, the refractive index and the dielectric constant are in the relation:

(refractive index)$^2$=dielectric constant and, hence, it is also possible to make substitution by either one as the case may be. For a transparent substance, refractive index measurement by a refractive index meter is frequently employed. For a flat plate sample, various methods such as a method of obtaining the dielectric constant from the capacity of a plate capacitor, a method according to a microwave cavity resonator or a dielectric resonator and the like have been employed.

A method employing resonance of microwaves, utilizing such a principle that a resonance frequency shifts in correspondence to the dielectric constant, is directed to paper, a film, plastic, ceramic and rubber etc., and can be utilized regardless of presence/absence of optical transparency.

FIG. 1 illustrates a principle diagram of conventional dielectric constant measurement employing a microwave cavity resonator. It is a microwave resonator 6 comprising a microwave introduction part 2 on an end and a microwave sensing part 4 on another end while a portion between both end portions consists of a waveguide having a constant field vibrational direction. A slit 8 is provided on the resonator 6 in a direction perpendicularly crossing the axis of the resonator 6 on the position of a loop of standing waves. A sample 10 is arranged in the slit 8 and microwaves are introduced from the microwave introduction part 2, for detecting the microwave intensity by the microwave sensing part 4. The dielectric constant is measured from the amount of displacement between a resonance frequency without arranging the sample 10 in the slit 8 and a resonance frequency at the time of not arranging the sample (refer to Japanese Patent Publication Gazette No. 3-38632).

A method of measuring a dielectric constant with microwave dielectric resonators is shown in FIG. 2. FIG. 2 is a sectional view showing a conventional orientation measuring device employing dielectric resonators. Referring to the figure, it comprises a pair of dielectric resonators 12a and 12b opposed through a sample 10, for making the dielectric resonators 12a and 12b generate field vectors having a single direction parallel to the surface of the sample 10 by a pair of antennas 14a and 14b oppositely arranged on side portions of the first dielectric resonator 12a through the dielectric resonator 12a and measuring the dielectric constant from the resonance characteristics thereof (refer to Japanese Utility Model Laying-Open Gazette No. 3-70368). Here, the antennas 14a and 14b are in the form of loops.

In the measuring device shown in FIG. 1 or FIG. 2, the cavity resonator or the dielectric resonators hold the sample 10 and are oppositely arranged on both sides thereof, and hence the shape of the measured sample 10 is limited to a sheetlike one. However, in the recent plastic molding field, the necessity for measuring the dielectric constant of molded plastic or its anisotropy has become strong. For example, in a resin molding of an electrical appliance such as a PC and a television set, or a plastic vessel such as a PET bottle, the dielectric constant or its anisotropy remarkably varies with positions due to flowability distribution, pressure distribution or the like in molding, which has come into question. Therefore, measurement of the dielectric constant or its anisotropy of a three-dimensional article is in demand.

The refractive index of a liquid is currently measured by an optical method, and the sugar level of fruit juice, the degree of fatigue of oil, the concentration of soy sauce or the like may also be managed with this refractive index. However, with this method, there is a problem that it is difficult to measure an opaque liquid such as heavy oil that can hardly transmit light There is also such a problem that only a substance of which refractive index is up to 1.52 at the maximum can be measured by the optical method from a critical angle in total reflection of light

DISCLOSURE OF THE INVENTION

An object of the present invention is to make it possible to measure dielectric constants not only in a sheetlike sample but also in a sample such as a three-dimensional molding and a liquid sample.

An aspect of a dielectric constant measuring method according to the present invention includes the following steps:

(step 1) a step of arranging a sample measuring face of a single dielectric resonator arranged only on one side of a sample under a fixed condition on a standard sample of which dielectric constant is known, properly varying either one or both (referred to as "the dielectric constant and/or the thickness") of the dielectric constant and the thickness of the standard sample for measuring a variance in the resonance frequency of the dielectric resonator with respect to each dielectric constant and/or thickness and acquiring a calibration curve in the variance of the resonance frequency responsive to the dielectric constant and/or the thickness.

(step 2) a step of measuring a variance of the resonance frequency by the dielectric resonator under the fixed condition as to a measured object sample of which the thickness is known.

(step 3) a step of obtaining the dielectric constant of the measured object sample from the measured value. and the calibration curve.

Another aspect of the dielectric constant measuring method is a dielectric constant measuring method arranging a sample measuring face of a single dielectric resonator arranged only on one side of a sample under a fixed condition on a measured object sample of which the thickness is. known, measuring a resonance frequency and obtaining the dielectric constant of the measured object sample according to the following equation (1):

$$\beta_g L 32\ \pi/2 + P\pi + \tan^{-1}(\alpha_2/\beta_g)\cdot\tan h[\tan h^{-1}(\alpha_3/\alpha_2) + \alpha_2 L_2] \quad (1)$$

$$\alpha_2 = (k_c^2 - \omega_0^2 \epsilon_0 \mu_0 \epsilon_s)^{1/2}$$

$$\alpha_3 = (k_c^2 - \omega_0^2 \epsilon_0 \mu_0)^{1/2}$$

$$\beta_g = (\omega_0^2 \epsilon_0 \mu_0 \epsilon_r - k_c^2)^{1/2}$$

where $\epsilon_s$ represents the dielectric constant of the sample, $\epsilon_r$ represents the relative dielectric constant of the dielectric resonator, L represents the thickness of the dielectric resonator, $\epsilon_0$ represents the dielectric constant of a measuring atmosphere. (air), $\mu_0$ represents the magnetic permeability of the measuring atmosphere, $\omega_0$ represents a microwave resonance angular frequency, $L_2$ represents the thickness of the measured object sample, $k_c$ represents a constant (eigenvalue) determined by the shape of the dielectric resonator, an electromagnetic field mode or the like, and P represents 0, 1, 2, 3, ... (these numerals mean integral times $\lambda_g/2$ in the axial direction).

Here, "a fixed condition" refers to operation of performing measurement while bringing the sample measuring face of the dielectric resonator into contact with the sample, or performing measurement while separating the sample measuring face of the dielectric resonator from the sample by a fixed distance.

In the dielectric constant measuring method according to the present invention, the resonance mode of the dielectric resonator is preferably such a mode that evanescent waves exude from the inner part of the dielectric resonator by resonance onto the side of the sample measuring face of the dielectric resonator.

If it is such a mode that field vectors of the evanescent waves are substantially parallel to one direction in such a resonance mode, the dielectric constant of the sample in the parallel direction can be measured.

In the dielectric constant measuring method according to the present invention, it is possible to use a cylindrical resonator and also to use a square resonator as the dielectric resonator.

In the dielectric constant measuring method according to the present invention, such a structure can be preferably employed that antennas of an exciter and a detector of the dielectric resonator are stick-shaped rod antennas arranged in a direction perpendicular to the sample measuring face of the dielectric resonator, the sample measuring face being close to or in contact with the sample.

In the aforementioned dielectric constant measuring method, such a structure can be preferably employed that the periphery of the dielectric resonator is covered with a shielding vessel except the sample measuring face.

In the aforementioned dielectric constant measuring method, the measurement sample can be measured also when the same is a liquid.

A dielectric constant measuring device according to the present invention comprises a single dielectric resonator arranged only on one side of a sample, a memory device made to store a calibration curve as to a variance of a resonance frequency measured by the dielectric resonator with respect to each thickness while varying the thickness of a standard sample of which dielectric constant is known and a data processor operating the dielectric constant of a measured object sample from a result of measurement of the variance of the resonance frequency of the measured object sample and the calibration curve.

[Measurement Principle]

FIG. 3 is a general model diagram in a case of bringing a sample 10 into contact with a dielectric resonator 20. According to this figure, schematic description is now made with reference to an electromagnetic field mode mainly used for measurement in a case of expressing the. resonance state of a dielectric resonator in a numerical formula. Assuming that dielectric substances of the dielectric resonator and the sample have no loss, a resonance frequency $f_0$ is obtained from $\omega_0 = 2\pi f_0$ satisfying the following equation:

$$\beta gL = \pi/2 + P\pi + \tan^{-1}(\alpha_3/\beta g) \cdot \tan h[\{\tan h^{-1}(\alpha_3/\alpha_2) \cdot \cot h\alpha_3 L_3\} + \alpha_2 L_2] \quad (A)$$

$\alpha_2$, $\alpha_3$ and $\beta g$ represent constants in a case of employing each area as a waveguide, while $\alpha_2$ and $\alpha_3$ are damping coefficients and $\beta g$ is a phase constant, which are expressed as follows:

$$\alpha_2 = (k_c^2 - \omega_0^2 \epsilon_0 \mu_0 \epsilon_s)^{1/2}$$

$$\alpha_3 = (k_c^2 - \omega_0^2 \epsilon_0 \mu_0)^{1/2}$$

$$\beta g = (\omega_0^2 \epsilon_0 \mu_0 \epsilon_r - k_c^2)^{1/2}$$

where $\epsilon_s$ represents the dielectric constant of the sample, $\epsilon_r$ represents the relative dielectric constant of the dielectric resonator, L represents the thickness of the dielectric resonator, $\epsilon_0$ represents the dielectric constant of a measuring atmosphere (air), $\mu_0$ represents the magnetic permeability of the measuring atmosphere, $\omega_0$ represents a microwave resonance angular frequency, $L_2$ represents the thickness of the measured object sample, $k_c$ represents a constant (eigenvalue) determined by the shape of the dielectric resonator, an electromagnetic field mode or the like, and P represents 0, 1, 2, 3, ... (these numerals mean integral times $\lambda_g/2$ in the axial direction). kc, which is determined by the shape of the dielectric resonator, the electromagnetic field mode, or the like, becomes as follows when the length and the width are "a" and "b" if the same can be regarded as a square magnetic wall:

$$k_{cmn}^2 = (m\pi/a)^2 + (n\pi/b)^2$$

"m" and "n" represent 0, 1, 2, 3, ... (these numerals mean integral times $\lambda/2$ in the sectional direction).

In the above equation (A), the measuring atmosphere is generally in the air in measurement, and an electric wall rightward beyond the measured object in the figure may be regarded as being at infinity, whereby coth $\alpha_3 L_3 \to 1$ in the case of $L_3 \to \infty$, and an equation (1) is obtained from the above equation (A).

$$\beta gL = \pi/2 + P\pi + \tan^{-1}(\alpha_2/\beta g) \cdot \tan h[\tan h^{-1}(\alpha_3/\alpha_2) + \alpha_2 L_2] \quad (1)$$

It is understood from the above relation that the resonance frequency varies if the dielectric constant $\epsilon_s$ of the sample or the thickness $L_2$ of the sample changes. That is, it indicates that the shifting quantity of the resonance frequency increases as compared with a blank time (where there is no measured sample) as the dielectric constant $\epsilon_s$ increases and the shifting quantity increases as the thickness $L_2$ increases. However, the strength of field vectors is at the maximum on the surface of the dielectric resonator and exponentially decreases as separating therefrom since evanescent waves are employed.

When solving this equation (1) in practice, it is easily obtained through a personal computer when mathematical software such as mathematical software sold under the trademark MATHEMATICA®, a U.S. registered trademark owned by Wolfram Research, Inc. of Champaign, Ill., is used. A measurement result having a small number of errors can be obtained by properly combining the aforementioned method of solving the equation and actually obtained calibration curve data.

While the above equation has been described with reference to the case of bringing the sample 10 into contact with the dielectric resonator 20, an equation is almost similarly obtained also when measuring the sample at a fixed interval from the sample measuring face of the dielectric resonator.

Therefore, when investigating the relation between the difference (assumed to be Δf) between the resonance frequency at the blank time and the resonance frequency at the time when the sample is arranged and forming a calibration curve, it follows that the dielectric constant of the sample can be measured merely by measuring the thickness and Δf. Also, depending on conditions, the dielectric constant of the sample can be obtained by solving the above equation (1).

FIG. 4 shows a block structural diagram of a measuring system of one Example of the present invention. It comprises a dielectric resonator 20 having a plane close to or in contact with a sample 10, a shielding vessel 26 substantially covering the dielectric resonator 20 except its sample measuring face, a microwave exciter 15 generating a frequency close to the resonance frequency of the dielectric resonator 20 at the time when the sample is present from an antenna 22a, a detector 16 detecting transmitted energy or reflected energy by the dielectric resonator 20 through an antenna 22b, a resonance frequency sensor 17 obtaining the resonance frequency from a variance of an output of the detector 16, and a computer 18 which is a data processor obtaining the dielectric constant of the sample 10 from the obtained resonance frequency. The computer 18 has a memory device 19 storing previously obtained calibration curve data or the like.

Microwaves are sent from the exciter 15 enabled to continuously vary the microwave frequency over a certain frequency range around the resonance frequency to the dielectric resonator 20, and the transmitted microwave intensity is sensed by the detector 16. This signal is sent to the resonance frequency sensor 17 in which the resonance frequency is measured, and this is sent to the computer 18. Calibration curve data of various dielectric constants and sample thicknesses are stored in the memory device 19, and the dielectric constant of the sample 10 is calculated from the calibration curve data and the measured resonance frequency by an extrapolation operation or the like.

While an example using calibration curve data has been described with reference to the above example, the dielectric constant of the sample can also be obtained by an operation by solving the equation (1) with the computer 18. In this case, it is also possible to obtain the dielectric constant of the sample while reducing errors in the operation process for the equation (1) with the calibration curve data.

While the antennas of the microwave exciter and the detector may be those in the forms of loops or rods, stick-shaped rod-shaped ones are. superior in homogeneity of field vectors in the in-sample plane and, hence, more preferable than loop-shaped ones as the antennas when the dielectric resonator are squared. At this time, the rod-shaped antennas are preferably arranged in a direction perpendicular to a plane of the dielectric resonator, the plane being close to or in contact with the sample.

[Embodiment 1 of the Invention]

FIG. 5 shows structural diagrams of a dielectric resonator according to one Example of the present invention. It follows that the dielectric resonator 20 is connected to the measuring system shown in FIG. 4. When detecting transmitted energy by the detector, the exciter and the detector are connected to the respective ones of the pair of antennas 22a and 22b oppositely arranged through the dielectric resonator 20.

FIG. 5 shows a sectional view (a) of an exemplary dielectric resonator including antennas and a top plan view (b) thereof. Referring to the figure, the microwave rod antennas (or loop antennas) 22a and 22b are arranged on positions and in a direction shown in the figure with respect to the dielectric resonator 20, so that the dielectric resonator 20 can be resonated while such a resonance mode can be formed that there are field vectors exuding outward from the dielectric resonator 20. While there is a TM mode, a TE mode and the like as the resonance mode, FIG. 5 expresses a $TM_{101}$ mode. While the strength of field vectors 24 almost exponentially decreases as separating from the dielectric resonator 20, the sample is placed at a short distance from the dielectric resonator 20 or in contact with the dielectric resonator 20 so that the resonance frequency shifts by electromagnetic coupling in response to the dielectric constant of the sample.

Because the field vectors become parallel on the dielectric surface and in the inner part of the sample in the case of this resonance mode, it becomes possible to measure the dielectric constant in the direction of the vectors. Therefore, anisotropy of the dielectric constant on the position can also be measured by turning the dielectric resonator 20 at a set angle around a rotation axis perpendicular to the sample surface using some sort of method and measuring the dielectric constant at each time.

The aforementioned arrangement, shapes etc. of the microwave rod antennas (or loop antennas) 22a and 22b with respect to the dielectric resonator 20 are not restricted to these but any arrangement and shapes may be employed so far as the dielectric resonator 20 can be resonated and such a resonance mode can be formed that there are field vectors exuding outward from the dielectric resonator 2. In the Example of FIG. 5, a square resonator is used for the dielectric resonator 20, and the rod antennas 22a and 22b are used as the antennas. Field vectors having the most excellent homogeneity can be obtained by thus combining a square resonator and rod antennas.

The periphery of the dielectric resonator 20 is preferably covered with the shielding vessel 26 except the sample measuring face in consideration of improvement in sensitivity etc. Thus, the Q value of a resonance curve can be increased. The shielding vessel is generally made of a conductive material such as a metal.

[Embodiment 2 of the Invention]

When there is no need to obtain information of anisotropy of a dielectric constant, i.e., when an average dielectric constant of a sample is to be measured dissimilarly to the example described in the embodiment 1 of the present invention, it is preferable to employ not a square but cylindrical dielectric resonator. The positions and the direction of mounting antennas are taken into consideration thereby making resonance, e.g., in a $TE_{01\delta}$ or $HEM_{21\delta}$ mode to enter such a field mode that exuding evanescent waves are in the form of a loop or not unidirectionally biased as shown in FIG. 6 on the sample surface, and the average dielectric constant can be measured. FIG. 6 is a diagram showing field distribution on the dielectric resonator surface in the $HEM_{21\delta}$ mode in the case of requiring no measurement of anisotropy, and a circle shown by a solid line in the figure shows the upper surface of the cylindrical dielectric resonator.

The present invention utilizes the evanescent waves exuding outward from the dielectric resonator in the aforementioned manner, for measuring the dielectric constant

[Embodiment 3 of the Invention]

It has been considered effective to further increase sharpness (Q value) of resonance in the first place for sharpening a resonance curve, in order to further improve the sensitivity of a dielectric resonator. Therefore, the inventors have made various trials.

Consequently, It has been found that it is effective to properly increase the distance between surfaces other than a sample measuring face and a shielding vessel. The optimum value thereof has also been found.

As to this value, the distance between the bottom surface (surface opposed to the sample measuring face) of the dielectric resonator and the shielding vessel was concretely 0.2 to 0.8 mm, preferably 0.3 to 0.6 mm. The distance between a side surface of the dielectric resonator and the shielding vessel was 2 to 5 mm, preferably 1 to 3 mm in the case of using a rod antenna as an antenna on the side surface not provided with the rod antenna. It was substantially similar also on the side surface provided with the rod antenna. However, it was more preferable that the distance on the side surface provided with the rod antenna was narrower than the distance on the side surface provided with no antenna. The above numerical values also depend on a used frequency and the dimensions of the dielectric resonator, and the degrees of the aforementioned values are conceivably preferable at the degrees of the bottom surface (30 mm×20 mm) and the height (20 mm) which are current dimensions. It is conceivably preferable to reduce the distances by more when these dimensions decrease by more or the used frequency exceeds the currently used degrees of gigahertz. In any case, it is preferable that the dielectric resonator and the shielding vessel are not in contact with each other.

It has been recognized that the Q value is remarkably improved by inserting a substance having a small dielectric loss factor such as polytetrafluoroethylene (PTFE) or quartz between the surfaces where the bottom surface (surface opposed to the sample measuring face) of the dielectric resonator opposed to the sample measuring face and the shielding vessel are opposed, to enable correct measurement of the resonance frequency. While it is preferable that the distances can be kept in such a state that the spacer is as small as possible or absent if possible, a flat plate of several mm square or a disk of several mm in diameter was used in practice.

It has also been recognized that the Q value is increased by optimizing the length of the rod antenna, and the distance to the dielectric resonator, etc.

Furthermore, as to preventing from intrusion of paper particles or liquid, it has been recognized that contamination with foreign matter can be prevented without substantially reducing the Q value by filling up a part or whole of a gap portion between the dielectric resonator and a metal with a substance (e.g., polytetrafluoroethylene) having a small dielectric constant and a small dielectric loss factor. Alternatively, it has also been recognized that a similar object can be attained also by covering the overall detection part with a thin sheet of a substance (e.g., polytetrafluoroethylene) similarly having a small dielectric constant and a small dielectric loss factor.

According to the present invention, the dielectric constant of the sample can be simply measured by merely measuring the resonance frequency when bringing the sample close to or in contact with the dielectric resonator.

This system is a sensing system from one side of the sample, whereby the measured sample does not have to be limited to a sheetlike dissimilarly to a conventional system, so even a thick block-shaped sample and a liquid sample can also be measured.

BRIEF DESCRIPTION OF THE DRAWINGS

FIG. 4 is a block structural diagram showing a measuring system of one Example of the present invention.

FIG. 15 shows diagrams showing an exemplary resonance mode ($TM_{201}$) in the embodiment, in which (A) is a diagram showing field vectors on a dielectric resonance surface in a plan view, and (B) is a diagram showing field vectors in the dielectric resonator on a position perpendicularly cut to pass through a spacer.

BEST MODES FOR CARRYING OUT THE INVENTION

The present invention is further specifically described on the basis of Examples.

EXAMPLE 1

Figure 1:
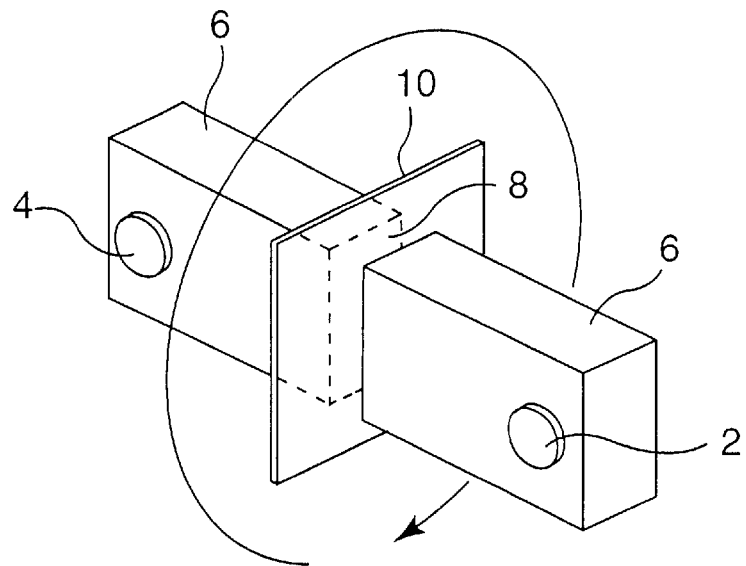
FIG. 1 is a schematic perspective view showing a conventional orientation measuring device employing a microwave cavity resonator.
Figure 2:
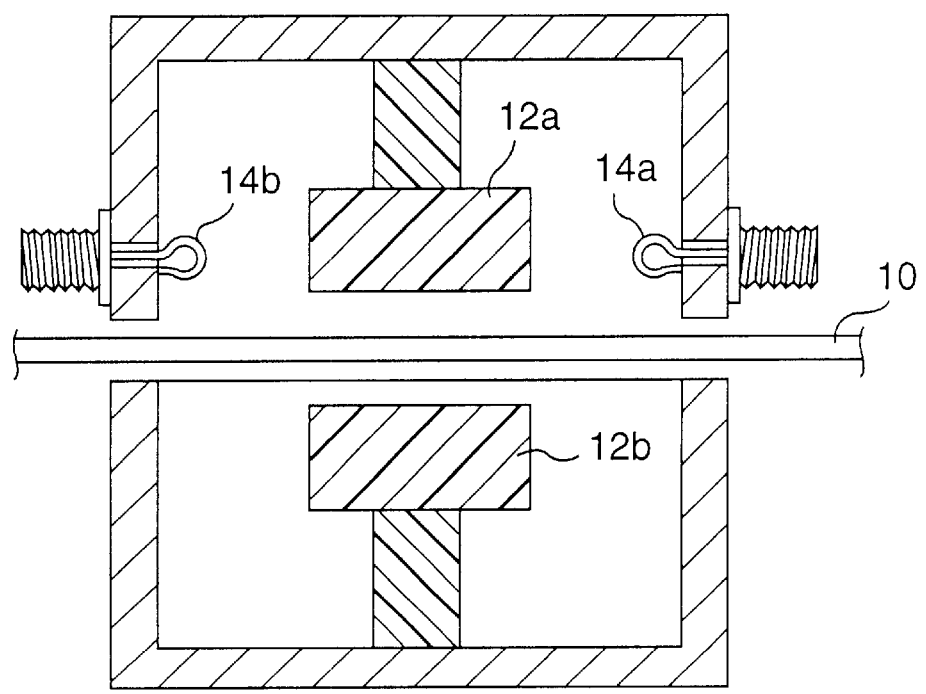
FIG. 2 is a sectional view showing a conventional orientation measuring device employing dielectric resonators.
Figure 3:
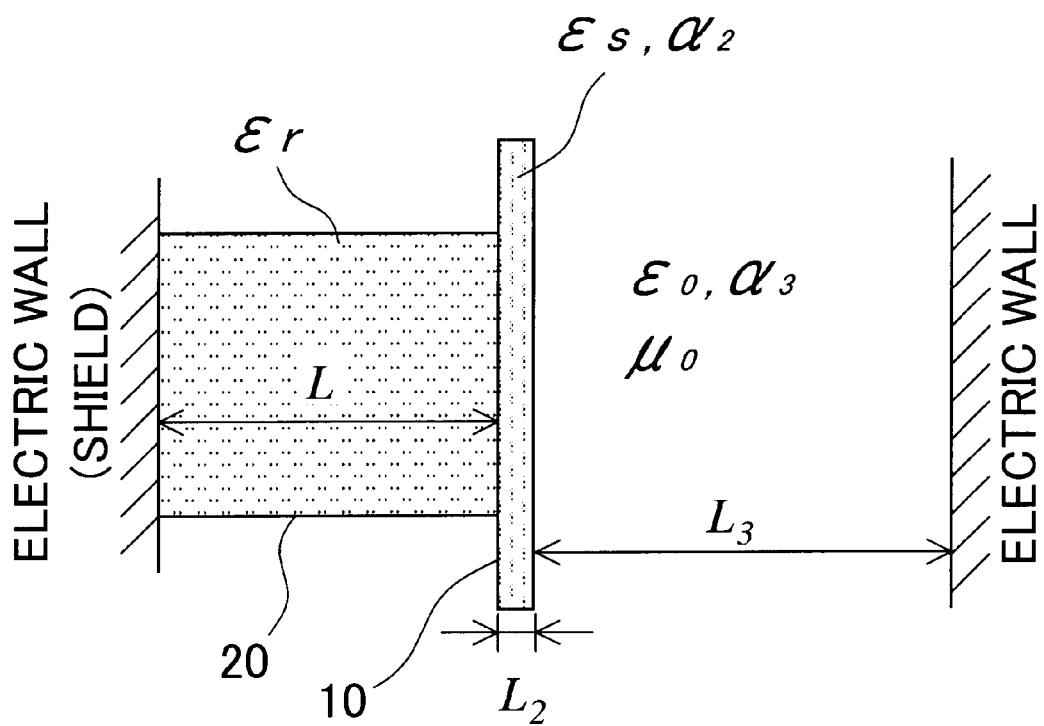
FIG. 3 is a general model diagram in a case of bringing a sample into contact with a dielectric resonator.
Figure 5A:
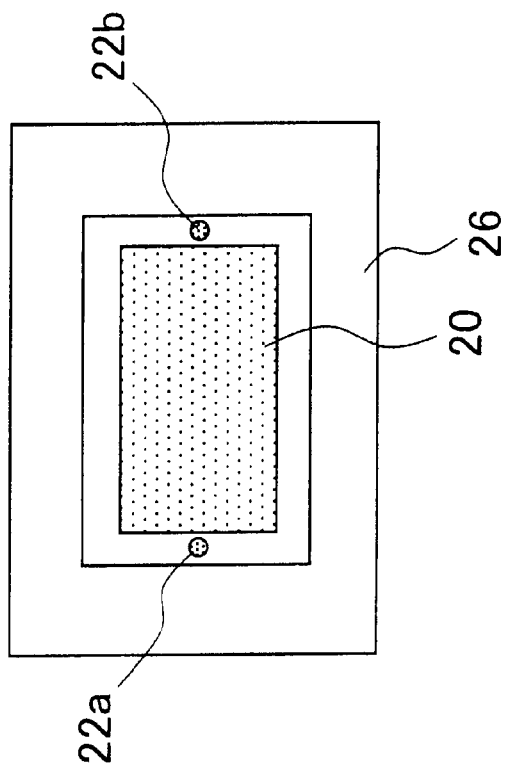
FIG. 5 shows structural diagrams of a dielectric resonator of one Example of the present invention, which are a sectional view (a) of an exemplary dielectric resonator including antennas and a top plan view (b) thereof.
Figure 5B:
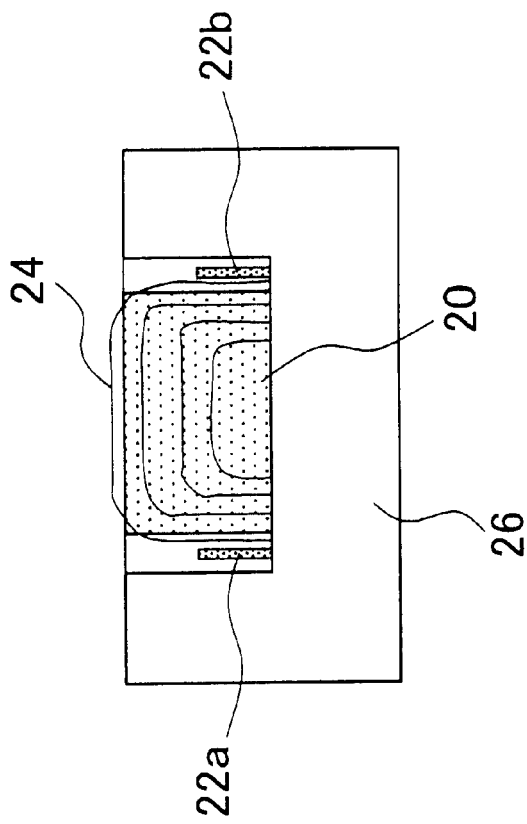
Figure 6:
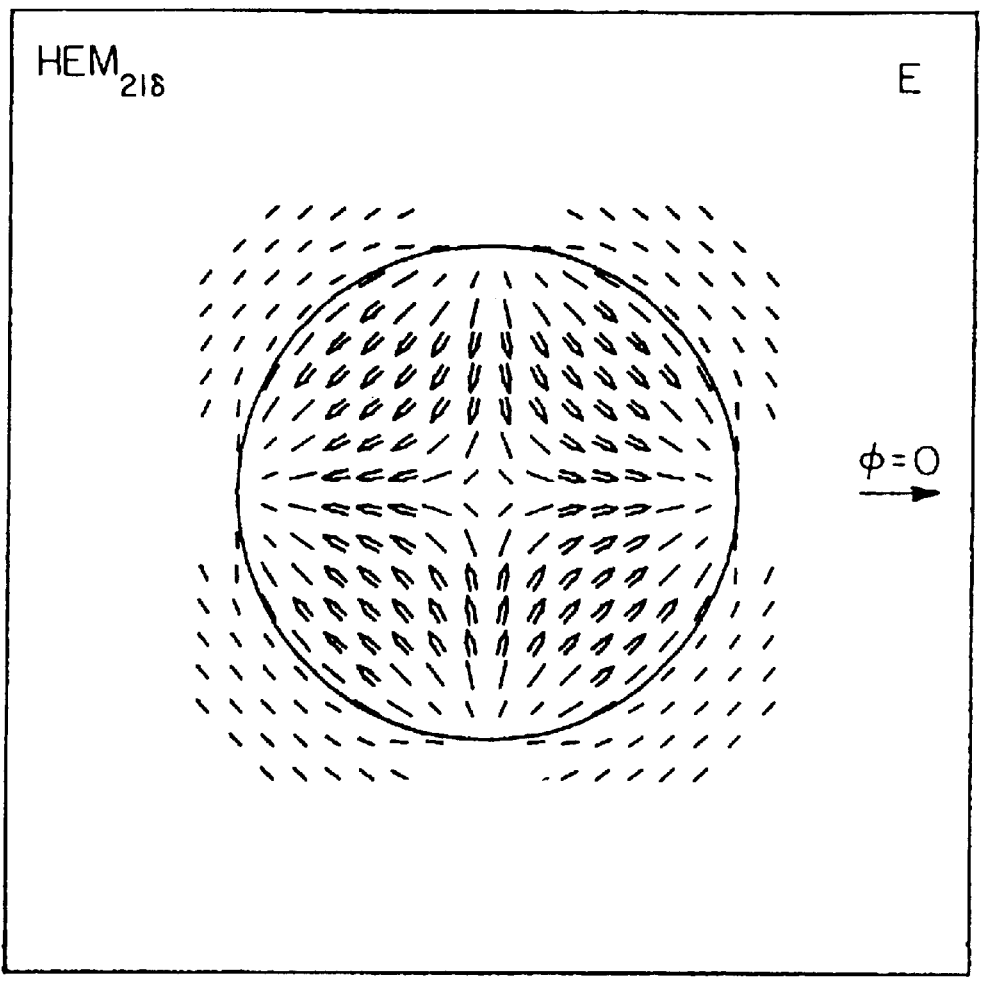
FIG. 6 is a diagram showing field distribution on a dielectric resonator surface in a $HEM_{21\delta}$ mode in the case of requiring no anisotropy measurement
Figure 7:
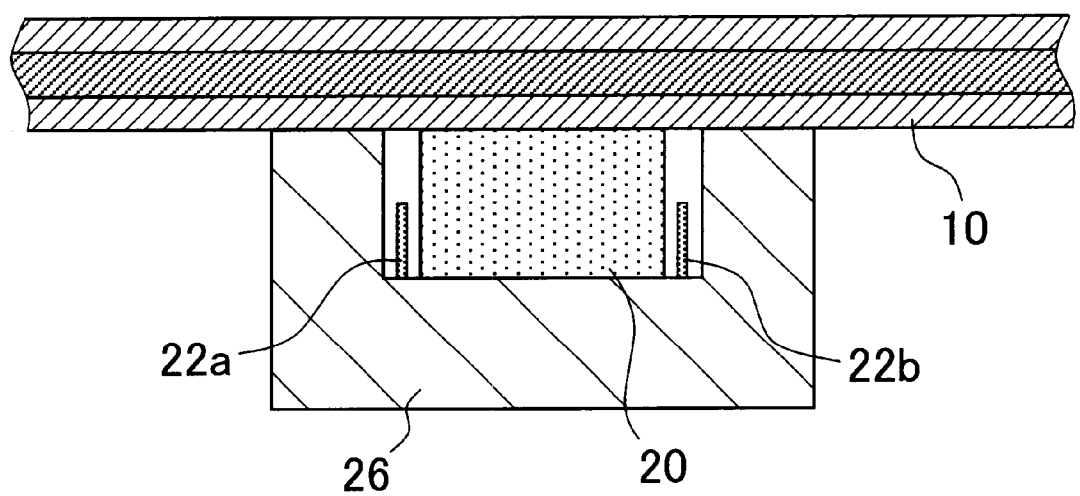
FIG. 7 is sectional view in a case of bringing a sample into contact with a dielectric resonator including antennas according to one Example of the present on and measuring the same.

FIG. 7 shows one Example of the present invention, exhibiting a sectional view in a case of bringing a sample into contact with a dielectric resonator and measuring the same. The dielectric resonator itself is identical in structure to that shown in FIG. 5. A square dielectric resonator 20 of 20.84 in dielectric constant is mounted with the bottom surface along the horizontal direction in a shielding brass vessel 26 of which the upper part is open. The dielectric resonator 20 is so set that its upper surface is substantially flush with an edge of the opening of the shielding vessel 26, and a sample 10 is placed to block the opening of the shielding vessel 26. An excitation antenna 22a and a detection antenna 22b are rod antennas, which are set between the shielding vessel 26 and the dielectric resonator 20.

Figure 8:
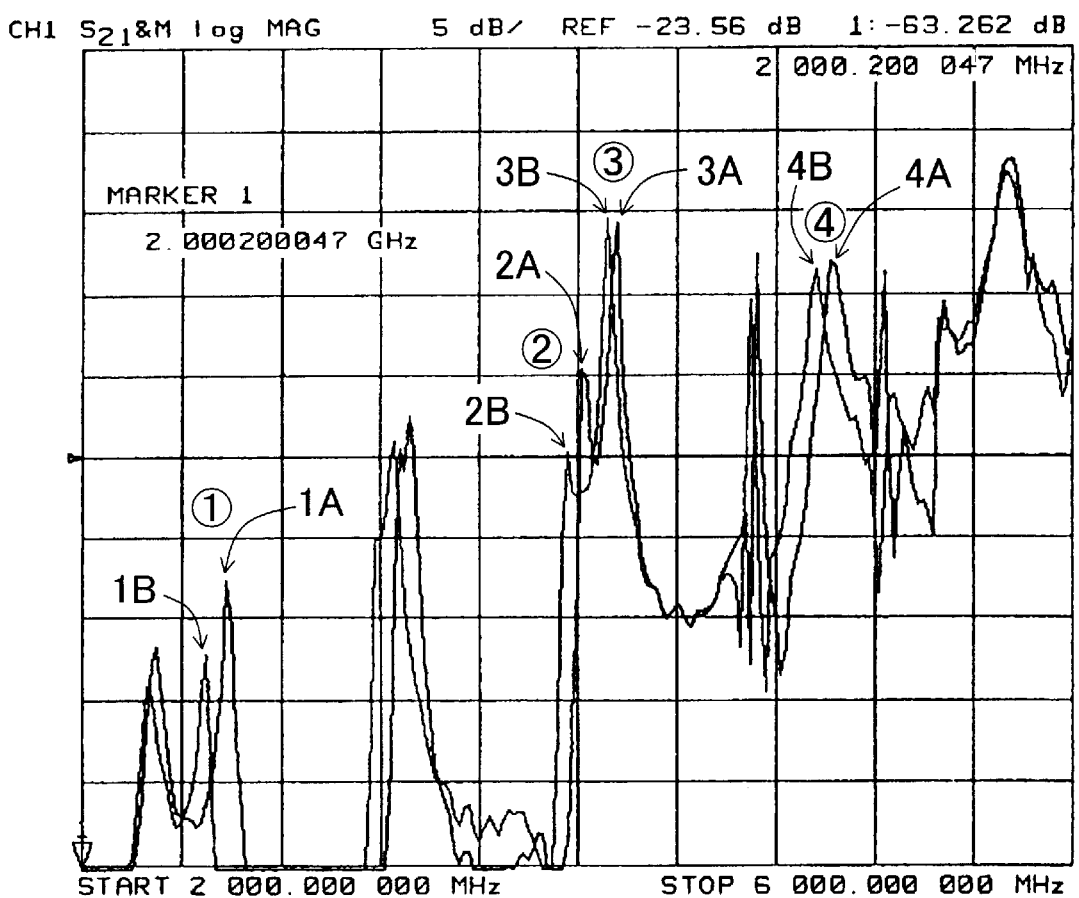
FIG. 8 is a waveform diagram showing a resonance spectrum in the case of placing a single polyethylene board on the dielectric resonator shown in FIG. 5.
Figure 9:
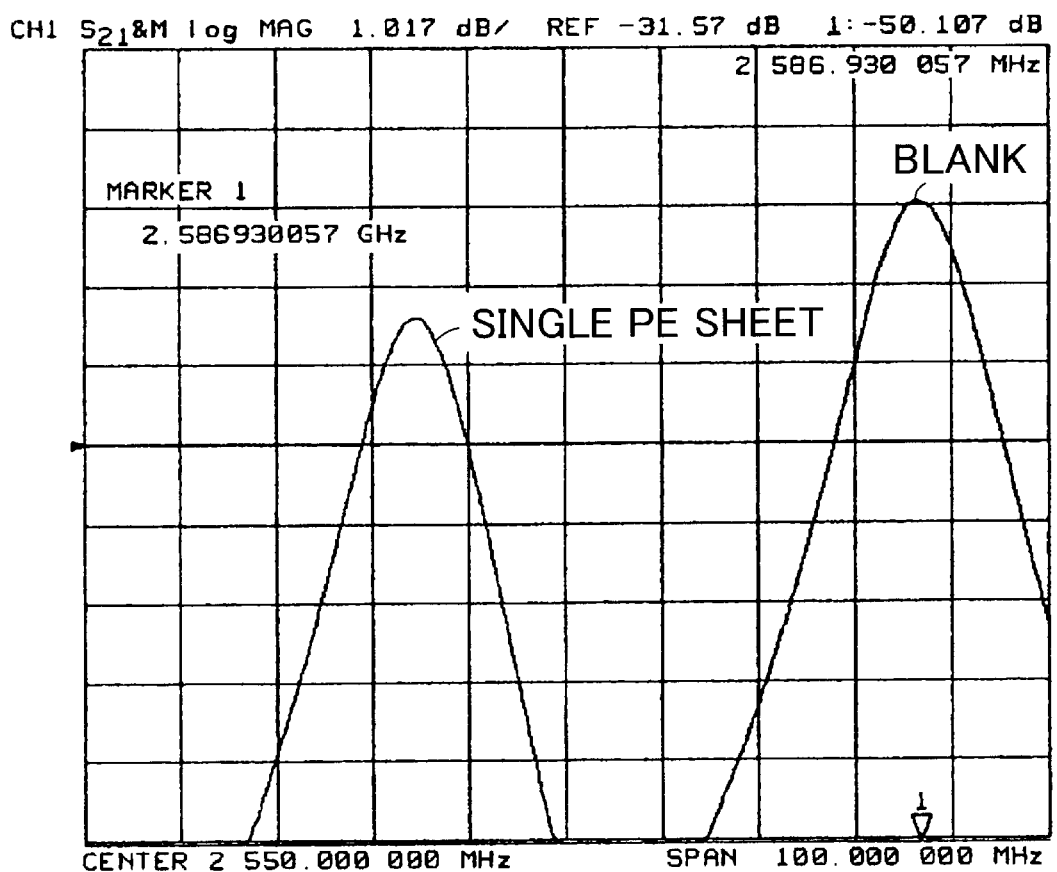
FIG. 9 is a diagram showing a peak ① in FIG. 8 in an enlarged manner, in which a right resonance curve, shows a blank time and the left shows a resonance curve in the case of placing the single polyethylene board.

Three polyethylene (PE) boards of 100 mm by 100 mm having a thickness of 2 mm as a sample 10 are brought into contact with this dielectric resonator 20. The antennas 22a and 22b of this resonator 20 were connected to the measuring system of the structure shown in FIG. 4 for making measurement FIG. 8 shows results obtained by measuring variances of transmission intensity in a case of varying a frequency from 2 GHz to 6 GHz with a network analyzer as part of raw data obtained by measurement FIG. 8 shows a resonance spectrum in a case of placing a single polyethylene board on the dielectric resonator 20. The horizontal axis shows the frequency (2 GHz to 6 GHz), and the vertical axis shows microwave transmission intensity. Each resonance peak corresponds to each resonance mode, and ① to ④ shown in FIG. 8 are peaks having relatively large variance widths of the resonance frequency. In the respective peaks of ① to ④, peaks of the resonance frequency at a blank time were shown with 1A, 2A, 3A and 4A, and peaks of the resonance frequency at the time of bringing the aforementioned single polyethylene board into contact were shown with 1B, 2B, 3B and 4B. When peak ① was employed out of the peaks ① to ④, the best detection sensitivity was exhibited in the relation between a frequency shifting quantity (the difference between the frequencies of peak 1A and peak 1B) and the dielectric constant of the sample and the thickness of the sample. FIG. 9 shows results obtained by measuring the resonance frequency at the blank time and the resonance frequency at the time of bringing the aforementioned single polyethylene board into contact on the same coordinates in peak ①. FIG. 9 is a diagram showing peak ① in FIG. 8 in an enlarged manner, in which the right resonance curve shows the blank time, and the left shows a resonance curve in the case of placing a single polyethylene board.

Figure 10:
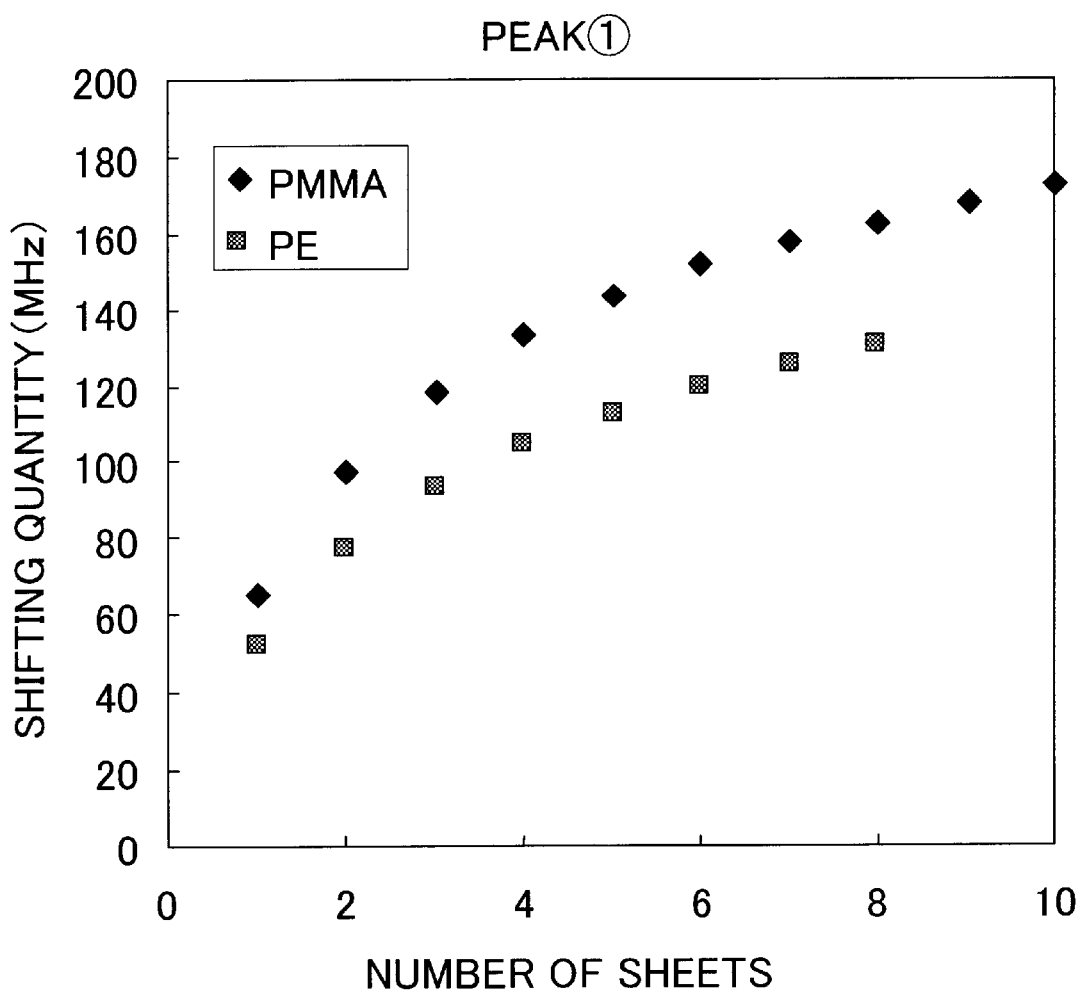
FIG. 10 shows results obtained by measuring the relation between a shifting quantity and a number of sheets as to each board of PMMA and PE with the peak ① FIG. 8.
Figure 11:
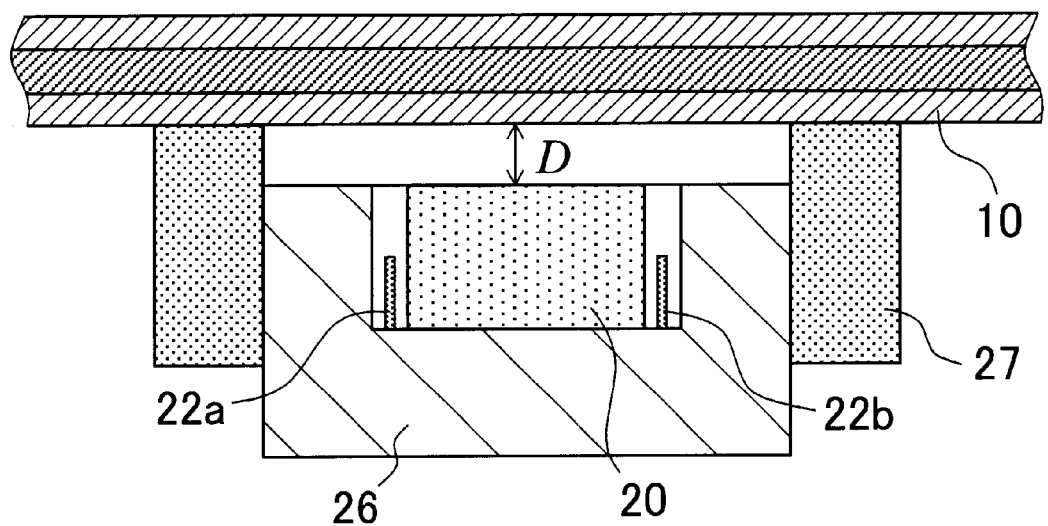
FIG. 11 is a sectional view showing an exemplary measuring device approximating a sample and a dielectric resonance to each other at a fixed interval for making measurements.

FIG. 10 shows variances of the shifting quantity (the resonance frequency at the blank time the resonance frequency at the time of placing the sample) with respect to the number of sheets at peak ① when preparing polyethylene boards and acrylic (PMMA) boards of 100 mm×100 mm in size and 2 mm in thickness and horizontally overlapping the same on the aforementioned dielectric resonator one for each. FIG. 10 is a diagram showing results obtained by measuring the relation between the resonance frequency shifting quantity and the number of sheets (thickness) as to each board of PMMA and PE with peak ① of FIG. 8. Variances of PMMA and PE result in different curves due to the difference between the dielectric constants of the respective materials. That is, the shifting quantity enlarges in PMMA having a larger dielectric constant Therefore, it is understood that the dielectric constant of an unknown measured sample can be measured by merely measuring the thickness of the unknown measured sample and measuring the resonance frequency shifting quantity when previously measuring a plurality of sheets of which the dielectric constants and thicknesses are known and preparing a plurality of calibration curves such as that shown in FIG. 10 while varying dielectric constants and thicknesses. That is, when calibration curves are obtained as to various materials having dielectric constants between those of PE and MA in FIG. 10 for example, and if the resonance frequency shifting quantity of an unknown sample having a thickness corresponding to four sheets is for example 120 MHz, the dielectric constant can be calculated by observing which material's calibration curve having an intermediate dielectric constant the same is put on, or by extrapolating the same from a calibration curve close to the measured value if there is no calibration curve on which the measured value is put When previously obtaining this calibration curve in a state arranging the sample on a position approximated to the face of the dielectric resonator 20 at a fixed interval, measurement is enabled also in a state where the sample 10 and the sample measuring face of the dielectric resonator 20 are not in contact with each other. FIG. 11 shows a sectional view of an exemplary measuring device making measurement while approximating the sample 10 and the dielectric resonator 20 to each other at a fixed interval D. Thus, measurement in a non-contact and non-destructive state is enabled by providing a sample support member 27 so that the interval D between the sample 10 and the dielectric resonator 20 is regularly fixed.

When a measured surface of the measured sample is a simple curved surface or the like, it is also applicable in the case of the curved sample by calculating resonance frequency shifting quantities as to respective distances up to the dielectric resonator 20 for respective small portions of the measured sample through the aforementioned equation (1), comparing a value obtained by conclusively totalizing the same and a case of a plane, and performing correction on the basis of the result Also in this case, a method of previously performing actual measurement as to each curved surface and obtaining a calibration curve is also possible in various cases, as a matter of course.

A liquid as a sample can also be measured by the aforementioned non-contact measurement. In the case of measurement of a liquid, the dielectric loss factor is large and, hence, the sample measuring face is preferably separated from the liquid surface. At this time, it is conceivable that a liquid case or a cover for the sample measuring face intervenes between the liquid surface and the sample measuring face. A substance such as air of which the dielectric constant is close to 1 is preferably selected as the material for such a case or cover. While a method of setting the sample measuring face from above the liquid surface through air at a fixed interval is also conceivable, fluctuation or the like such as swinging of the liquid surface influences the measurement and hence a contrivance for reduction thereof becomes necessary. It is further preferable to increase the capacity of the case storing the liquid for reducing the influence on the measurement. It may simply be possible to measure the resonance frequency as described above, and hence neither transparency is required to the liquid sample nor a critical angle limits the range of dielectric constant (refractive index) measurement dissimilarly to an optical measuring method.

EXAMPLE 2

Figure 12A:
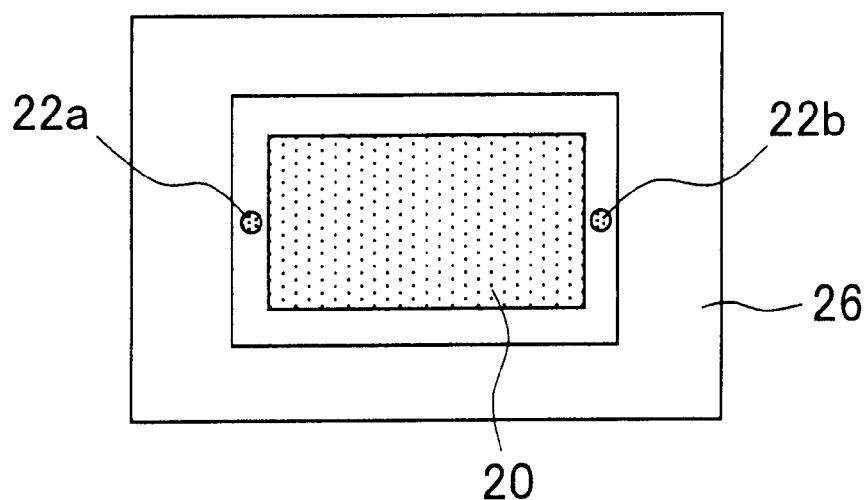
FIG. 12 shows diagrams showing an Example interposing a spacer between the bottom surface of a dielectric resonator and a shielding vessel, in which (A) is a plan view and (B) is a vertical sectional view of (A).
Figure 12B:
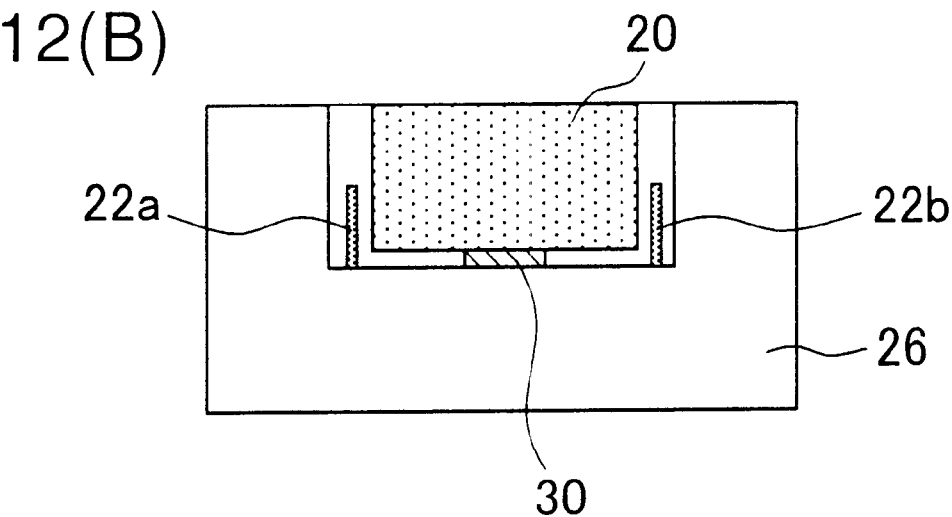
Figure 13A:
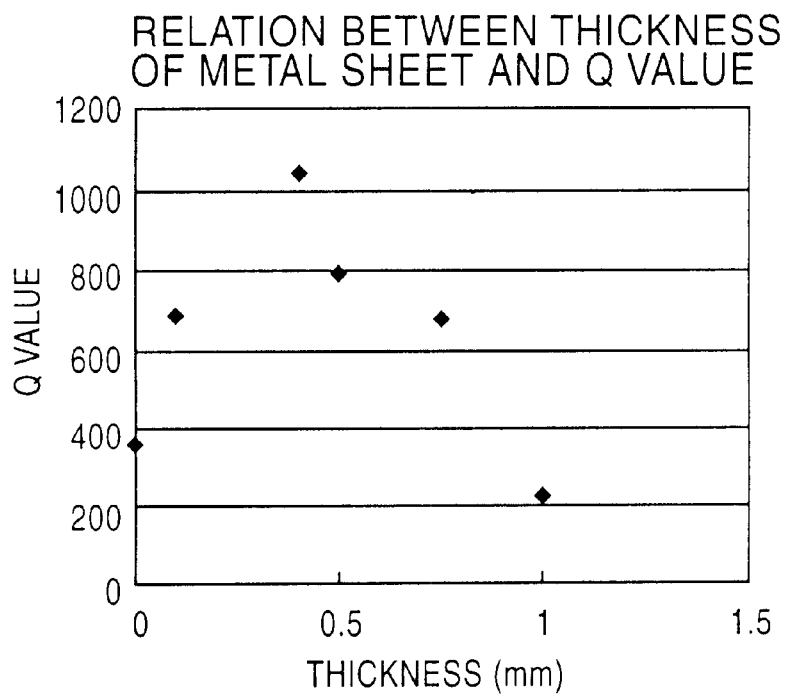
FIG. 13 shows diagrams showing the relations between the thicknesses of spacers and Q values in the Example, in which (A) shows a case where the spacer is a metal sheet, and (B) shows a case where the spacer is a PET film.
Figure 13B:
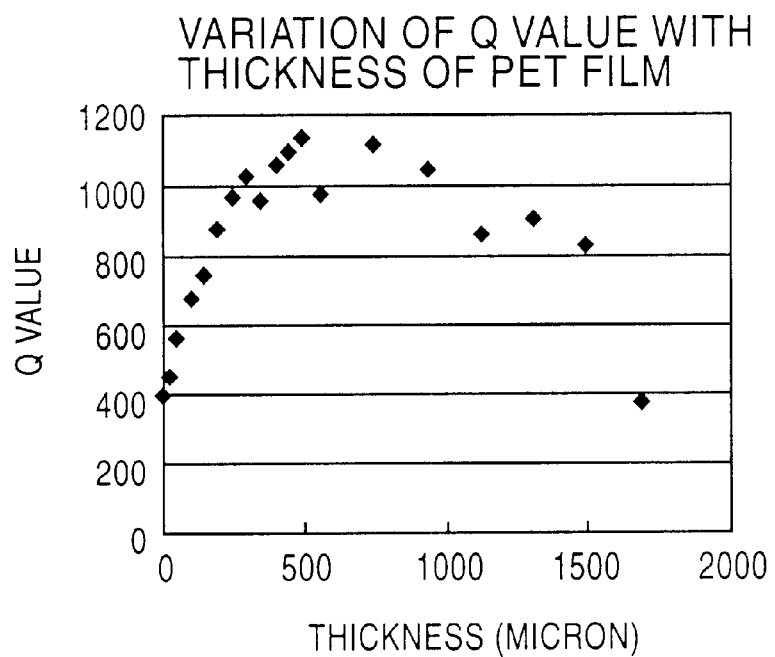

To improve the Q value (sharpness of resonance) of a dielectric resonator, a spacer 30 was interposed between the bottom surface of the dielectric resonator 20 and a shielding vessel 30, as shown in FIG. 12. Referring to FIG. 12, (A) is a plan view, and (B) is a vertical sectional view of (A). The relation between the thickness of the spacer 30 and the Q value varied as shown in FIG. 13 when making resonance of a $TM_{201}$ mode at 4 GHz. Referring to FIG. 13, (A) shows a case where the spacer 30 is a metal sheet, and (B) shows a case where the spacer 30 is a PET (polyethylene terephthalate) film. It is understood from these results that the thickness of the spacer 30 is optimally around 0.5 mm for improvement of the Q value.

Figure 14A:
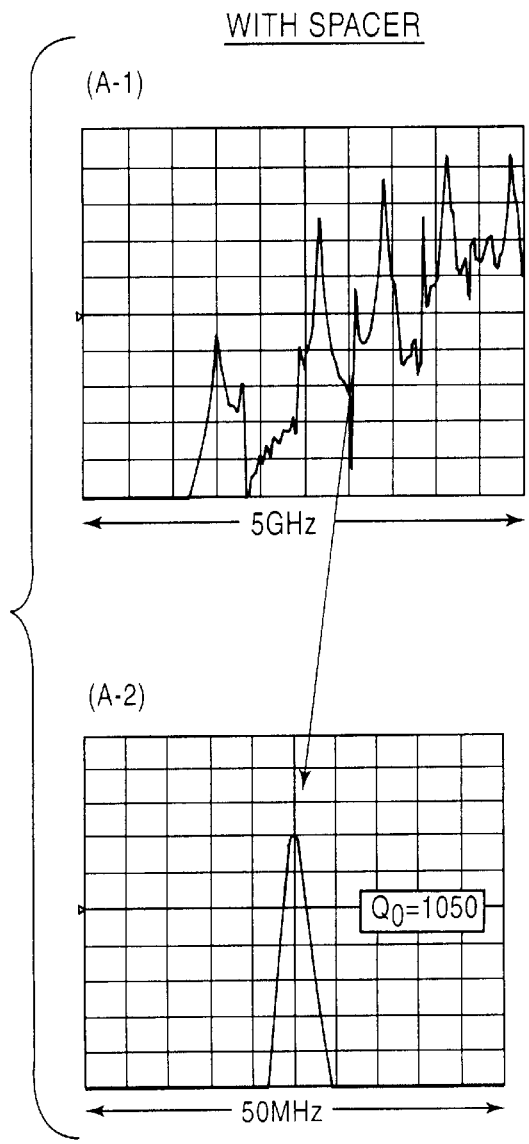
FIG. 14 shows diagrams showing differences between Q values responsive to presence/absence of a spacer in the Example, in which (A) shows a case where the spacer has been interposed, and (B) shows a case where no spacer has been interposed.
Figure 14B:
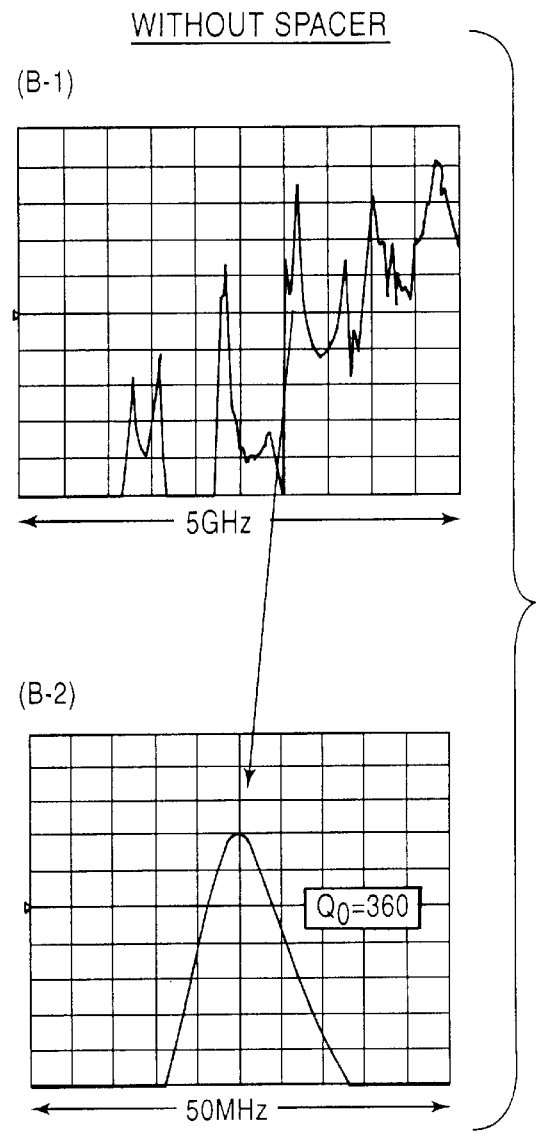

FIG. 14 shows results obtained by measuring the difference between Q values responsive to presence/absence of the spacer 30. The horizontal axis shows frequencies, and the vertical axis shows microwave transmission intensity. (A) shows a case of interposing the spacer 30, and (B) shows a case of bringing the bottom surface of the dielectric resonator 20 into direct contact with the shielding vessel 30 without interposing the spacer. In the respective figures, spectra (A-2) and (B-2) shown on the lower sides show peaks of the same frequency positions in respective spectra (A-1) and (B-1) while magnifying the horizontal axis to 100 times. When comparing (A) and (B) with each other, the Q value increases from 360 to 1050 due to the provision of the spacer 30. Thus, peak detection, i.e., measuring accuracy for the resonance frequency was remarkably improved.

While there are a metal, a high-polymer film and the like as the materials employed for the spacer, a quartz plate having small dielectric loss or the like is preferable.

While the spacer 30 can be arranged on a plurality of portions of the bottom surface of the dielectric resonator 20 to be subdivided on four corners of the bottom surface when the dielectric resonator 20 has, for example, a square shape, it was recognized that the Q value increases when a single spacer is placed on the central portion as shown in FIG. 12 rather than thus dispersing the same into a plurality of portions.

As a result, the spacer is preferably as small as possible. As a result of trials, the inventors have used a flat plate shaped spacer of several mm square or a discoidal spacer having a diameter of several mm.

Rod antennas 22a and 22b are preferably arranged substantially at centers of the dielectric resonator 20 and the metal wall of the shielding vessel 26 as shown in FIG. 12, while the length, having such a tendency that received microwave intensity increases but the Q value lowers if the same is elongated, is preferably set to about ½ to ⅔ of the height of the dielectric resonator 20. While the Q value increases as the thickness reduces, the thickness is preferably about 0.1 mm to 0.5 mm from the relation with respect to the intensity.

Such a resonance mode ($TM_{201}$) can be formed that all field vectors on the surface of the dielectric resonator 20 are parallel in the major axis direction as shown, for example, in FIG. 15, by interposing the spacer 30 between the central portion of the bottom surface of the dielectric resonator 20 and the shielding vessel 30 and properly defining a gap between the dielectric resonator 20 and the shielding vessel 26. (A) shows field vectors on the surface of the dielectric resonator 20 in a plan view, and (B) shows field vectors in the dielectric resonator 20 on a position cut in the vertical direction to pass through the spacer 30. While FIG. 15 omits illustrations of the rod antennas 22a and 22b, they are arranged similarly to FIG. 12. Such a resonance mode can be utilized for measuring anisotropy of the dielectric constant of the sample 10. Contamination with foreign matter can be prevented without substantially reducing the Q value by filling up the gap between the dielectric resonator 20 and the shielding vessel 26 with a substance 40 having a low dielectric constant and a low dielectric loss factor such as polytetrafluoroethylene, as shown in FIG. 16.

Figure 17A:
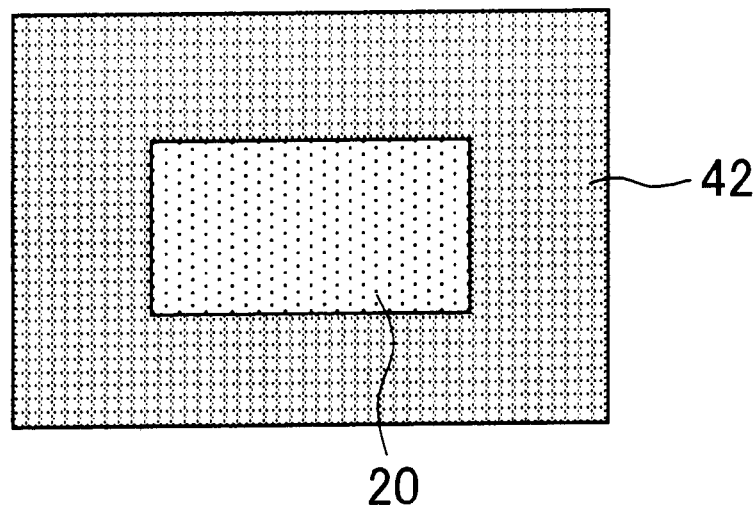
FIG. 17 shows diagrams showing an Example sealing a gap between a dielectric resonator and a shielding vessel, in which (A) is a plan view, and (B) is a vertical sectional view.
Figure 17B:
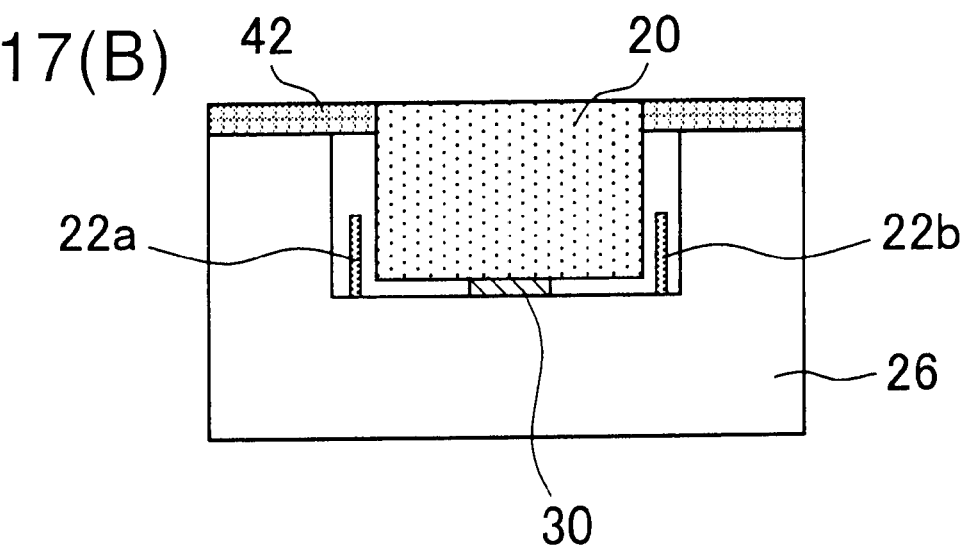

Furthermore, contamination with foreign matter can be prevented without substantially reducing the Q value by lowering the height of the shielding vessel 26 and substitutionally mounting a substance 42 having characteristics similar to those of the shielding vessel 26, as shown in FIG. 17. Referring to FIG. 17, (A) is a plan view, and (B) is a vertical sectional view.

Figure 18A:
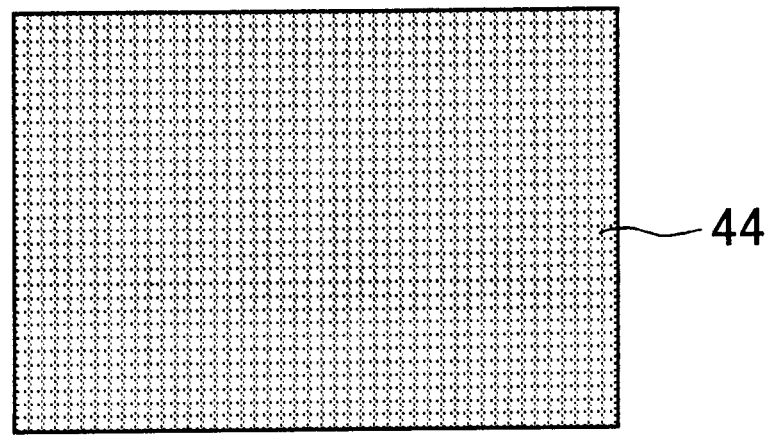
FIG. 18 shows diagrams showing another Example sealing a gap between a dielectric resonator and a shielding vessel, in which (A) is a plan view, and (B) is a vertical sectional view.
Figure 18B:
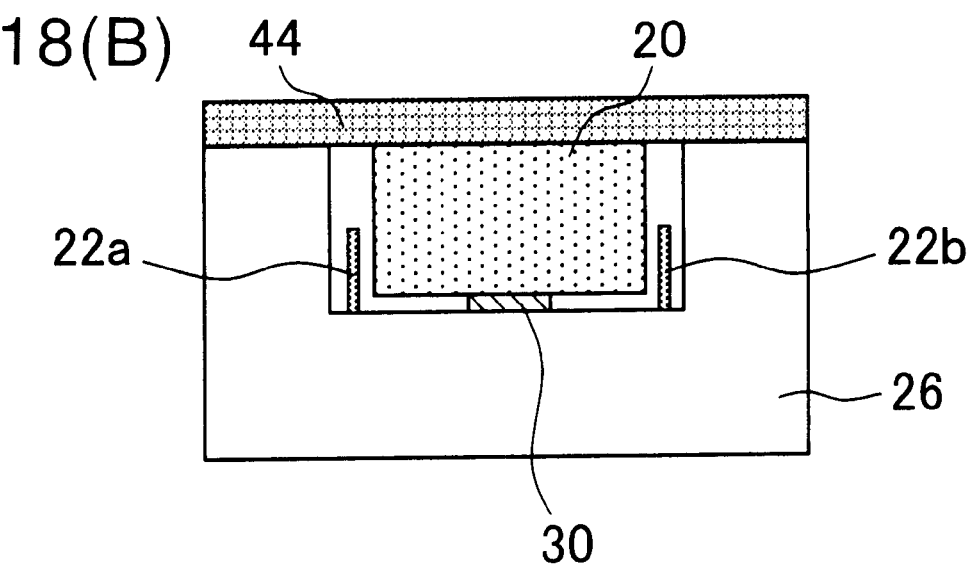

Furthermore, contamination with foreign matter can also be prevented by setting the upper surface of the dielectric resonator 20 to be substantially flush with the edge of the opening of the shielding vessel, and covering an overall sensor which includes the dielectric resonator 20, the edge of the opening of the shielding vessel 26 and the gap between the dielectric resonator 20 and the shielding vessel 26 with a sheet 44 of polytetrafluoroethylene26 as shown in FIG. 18.

Figure 16A:
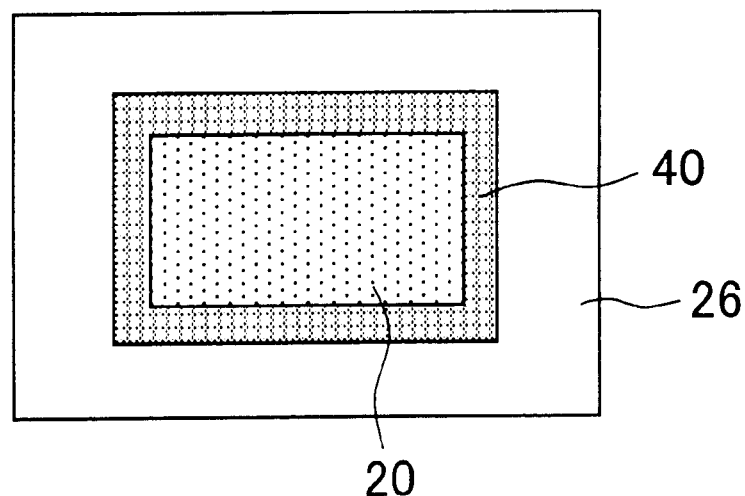
FIG. 16 shows diagrams showing an Example filling up a gap between a dielectric resonator and a shielding vessel, in which (A) is a plan view, and (B) is a vertical sectional view.
Figure 16B:
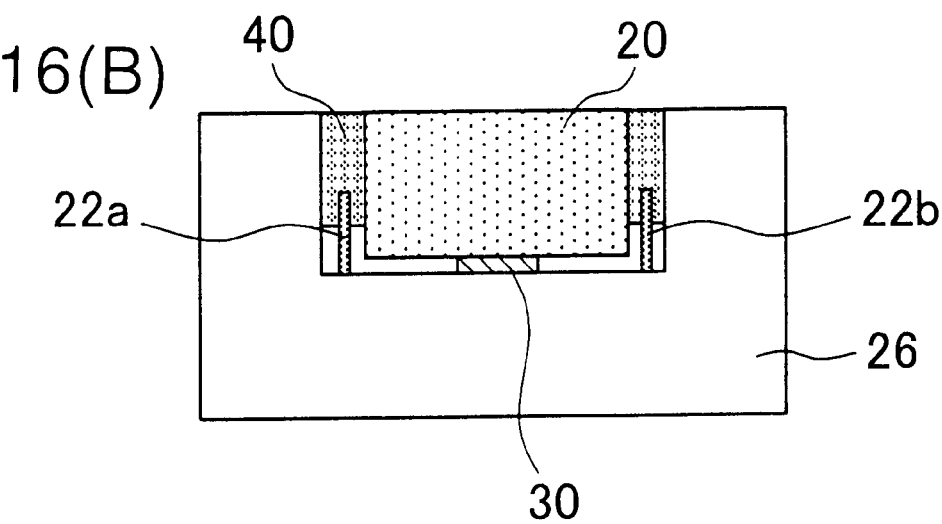

While the example directing the measuring face upward has been described in the aforementioned measuring systems shown in FIGS. 16, 17 and 18, the measuring surface may be used to be in the vertical direction or an oblique direction.

In the aforementioned measuring systems shown in FIGS. 16, 17 and 18, the spacer 30 between the bottom surface of the dielectric resonator 20 and the shielding vessel 26 does not have to be used while it is also possible to improve the Q value when holding the dielectric resonator 20 with the member 40, 42 or 44 of a substance having a low dielectric constant and a low dielectric loss factor, or mechanically holding the dielectric resonator 20 by using an adhesive.

In the measuring system shown in FIG. 12, it is also possible to arrange the side surfaces of the cylindrical or prismatic dielectric resonator 20 to be held and supported by spacers from both sides in place of the spacer 30 on the bottom surface. In this case, it is necessary to use an adhesive or provide the spacers with elastic force for supporting since it is necessary to support the dielectric resonator with the spacers. When arranging the dielectric resonator so that the measuring face is substantially in the vertical direction as a specific example in such a case, the spacer may simply support the same from below and there is no need to hold the dielectric resonator. In any case, it is further preferable that no antennas are arranged on the side surfaces supported by the spacers when supporting the dielectric resonator by the spacers from the sides of the side surfaces in the case of a prismatic dielectric resonator.

Figure 19A:
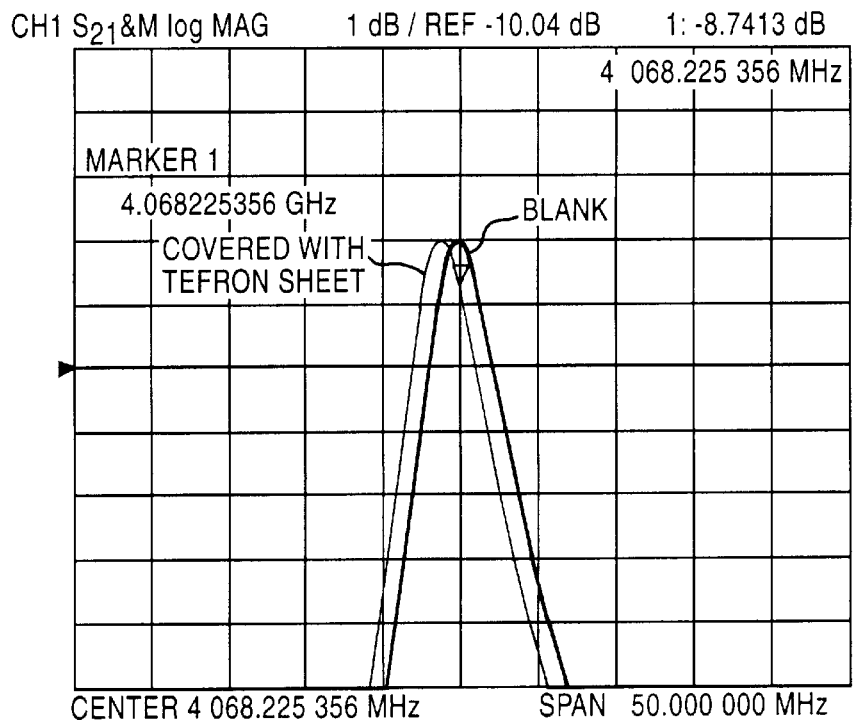
FIG. 19 shows diagrams showing characteristics of the Example of FIG. 18, in which (A) shows peaks of a microwave transmission strength spectrum in the case of covering with a polytetrafluoroethylene sheet (left) and the case without covering (right), and (B) shows a result (left) obtained by further placing a sample thereon and measuring the same.

FIG. 19(A) shows the same peaks of microwave transmission intensity spectra in the case of covering with a polytetrafluoroethylene sheet of 50 μm in thickness (left) and the case without covering (right). While shifts of resonance frequencies are observed due to variances of dielectric constants, the shapes of the peaks are substantially unchanged, and the Q values hardly decrease also in this case.

Figure 19B:
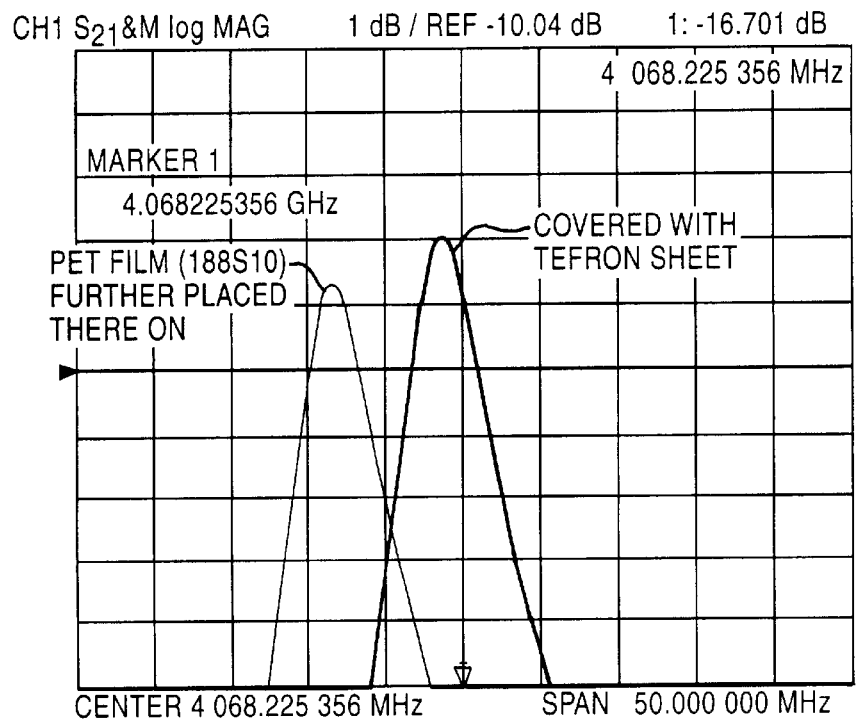

FIG. 19(B) shows results obtained by measuring shifts of resonance frequencies by covering an overall sensor with a sheet 44 of polytetrafluoroethylene and placing a PET film (188510) serving as a sample on the sheet 44 of polytetrafluoroethylene. The right peak shows a case of placing no sample while the left peak shows the case of placing the sample, and the dielectric constant of the sample can be measured by thus preventing foreign matter from coming into the gap between the dielectric resonator 20 and the shielding vessel 26.

Industrial Availability

According to the present invention, dielectric constants of sheetlike substances such as a high-polymer sheet and paper including films, and three-dimensional articles such as moldings of plastic, resin, rubber and the like, as well as liquids such as an aqueous solution, a water dispersion liquid, an organic solvent liquid, liquid organic matter and the like can be readily measured with microwaves.

What is claimed is:

1. A dielectric constant measuring method employing a dielectric resonator operation in such a resonance mode that evanescent waves exude from the inner part of the dielectric resonator toward a sample measuring face side and comprising the following steps for obtaining the dielectric constant of a sample to be measured:

(step 1) a step of arranging a sample measuring face of a single dielectric resonator arranged only on one side of a standard sample having a known dielectric constant under a fixed condition, appropriately varying the dielectric constant and/or the thickness of the standard sample for measuring a first change of the resonance frequency of the dielectric resonator with respect to each dielectric constant and/or thickness and acquiring a calibration curve of the first change of the resonance frequency depending on the dielectric constant and/or the thickness;

(step 2) a step of measuring a second change of the resonance frequency by the dielectric resonator under the fixed condition as to the sample to be measured having a known thickness; and (step 3) a step of obtaining the dielectric constant of the sample to be measured from the measured value and the calibration curve.

2. A dielectric constant measuring method arranging a sample measuring face of a single dielectric resonator arranged only on one side of a sample to be measured having a known thickness under a fixed condition and operating in such a resonance mode that evanescent waves exude from the inner part of the dielectric resonator toward a sample measuring face side measuring a resonance frequency and obtaining the dielectric constant of the sample to be measured according to the following equation (1):

$$\beta_g L = \pi/2 + P\pi + \tan^{-1}(\alpha_2/\beta_g) \cdot \tan h[\tan h^{-1}(\alpha_3/\alpha_2) + \alpha_2 L_2] \quad (1)$$

$$\alpha_2 = (k_c^2 - \omega_0^2 \epsilon_0 \mu_0 \epsilon_s)^{1/2}$$

$$\alpha_3 = (k_c^2 - \omega_0^2 \epsilon_0 \mu_0)^{1/2}$$

$$\beta_g = (\omega_0^2 \epsilon_0 \mu_0 \epsilon_r - k_c^2)^{1/2}$$

where $\epsilon_s$ represents the dielectric constant of the sample, $\epsilon_r$ represents the relative dielectric constant of the dielectric, resonator, L represents the thickness of the dielectric resonator, $\epsilon_0$ represents the dielectric constant of a measuring atmosphere (air), $\mu_0$ represents the magnetic permeability of the measuring atmosphere, $\omega_0$ represents a microwave resonance angular frequency, $L_2$ represents the thickness of the sample to be measured, $k_c$ represents a constant (eigenvalue) determined by the shape of the dielectric resonator, an electromagnetic field mode or the like, and P represents 0, 1, 2, 3, . . . (these numerals mean integral times $\lambda_g/2$ in the axial direction).

3. The dielectric constant measuring method according to claim 1 or 2, wherein the fixed condition is to perform measurement while bringing the sample measuring face of the dielectric resonator into contact with the sample.

4. The dielectric constant measuring method according to claim 1 or 2, wherein the fixed condition is to perform measurement while separating the sample measuring face of the dielectric resonator from the sample by a fixed distance.

5. The dielectric constant measuring method according to claim 1 or 2, wherein antennas of an exciter and a detector of the dielectric resonator are stick-shaped rod antennas arranged in a direction perpendicular to a plane of the dielectric resonator, the plane being close to or in contact with the sample.

6. A dielectric constant measuring device comprising:

a single dielectric resonator arranged only on one side of a standard sample or a sample to be measured and operating in such a resonance mode that evanescent waves exude from an inner part of the dielectric resonator toward a sample measuring face side;

a shielding vessel substantially covering the dielectric resonator except its sample measuring face;

a memory device made to store a calibration curve as to a change of a resonance frequency measured by the dielectric resonator with respect to each thickness while varying the thickness of the standard sample of which dielectric constant is known; and a data processor operating the dielectric constant of the sample to be measured from a result of measurement of the change of the resonance frequency of the sample to be measured and the calibration curve.

7. The dielectric constant measuring device according to claim 6, wherein the dielectric resonator is in the form of a prism or a cylinder, and the bottom surface of a single side of the cylinder or prism is employed as the sample measuring face.

8. The dielectric constant measuring device according to claim 6 or 7, wherein a clearance is provided between a surface other than the sample measuring face of the dielectric resonator and the shielding vessel.

9. The dielectric constant measuring device according to claim 8, providing a spacer between the bottom surface opposed to the sample measuring face and the shielding vessel.

10. The dielectric constant measuring device according to claims 8, providing a spacer between the side surface of the dielectric resonator and the shielding vessel.

11. An orientation measuring device comprising:

a single dielectric resonator arranged only on one side of a sample;

a shielding vessel substantially covering the dielectric resonator except its sample measuring face;

a memory device made to store a calibration curve as to a variance of a resonance frequency measured by the dielectric resonator with respect to each thickness while varying the thickness of a standard sample of which dielectric constant is known; and a data processor operating the dielectric constant of a sample to be measured from a result of measurement of the variance of the resonance frequency of the sample to be measured and the calibration curve, wherein filling or sealing at least part of a clearance between a surface other than the sample measuring face of the dielectric resonator and the shielding vessel with a substance of which dielectric constant and dielectric loss factor are small to be substantially flush with the sample measuring face to entirely include the outer edge portion of the sample measuring face.

12. The orientation measuring device according to claim 11, wherein the dielectric resonator is in the form of a prism or a cylinder, and the bottom surface of a single side of the cylinder or prism is employed as the sample measuring face.

* * * * *